US006635284B2

(12) United States Patent
Mehta et al.

(10) Patent No.: US 6,635,284 B2
(45) Date of Patent: *Oct. 21, 2003

(54) DELIVERY OF MULTIPLE DOSES OF MEDICATIONS

(75) Inventors: Atul M. Mehta, Ramsey, NJ (US); Andrew L. Zeitlin, Millington, NJ (US); Maghsoud M. Dariani, Fanwood, NJ (US)

(73) Assignee: Celegene Corporation, Warren, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 45 days.

(21) Appl. No.: 09/038,470

(22) Filed: Mar. 11, 1998

(65) Prior Publication Data

US 2003/0113373 A1 Jun. 19, 2003

Related U.S. Application Data

(60) Division of application No. 08/892,190, filed on Jul. 14, 1997, now Pat. No. 5,837,284, which is a continuation-in-part of application No. 08/567,131, filed on Dec. 4, 1995, now abandoned, and a continuation-in-part of application No. 08/583,317, filed on Jan. 5, 1996, now Pat. No. 5,733,756, and a continuation-in-part of application No. 08/647,642, filed on May 15, 1996, now abandoned.

(51) Int. Cl.[7] .............................. A61K 9/14; A61K 9/16; A61K 9/50; A61K 9/54; A61K 9/20

(52) U.S. Cl. ...................... 424/497; 424/458; 424/474; 424/468; 424/464; 424/490; 424/462; 424/494; 424/489; 424/480

(58) Field of Search ................................. 424/489, 497, 424/464, 462, 480, 494, 468, 474, 490, 458

(56) References Cited

U.S. PATENT DOCUMENTS

| 2,507,631 A | 5/1950 | Hartmann et al. .......... 260/294 |
| 2,957,880 A | 10/1960 | Rometsch .................... 546/233 |
| 4,137,300 A | 1/1979 | Sheth et al. ................... 424/21 |
| 4,794,001 A | 12/1988 | Mehta et al. ................ 424/458 |

(List continued on next page.)

FOREIGN PATENT DOCUMENTS

| CA | 1297368 | 3/1992 |
| FR | 2 635 460 | 9/1994 |
| WO | WO 93/05769 | 4/1993 |
| WO | WO 97/03671 | 2/1997 |

(List continued on next page.)

OTHER PUBLICATIONS

Angrist et al., *J. Clin. Psychopharm.*, 1992, 12(4), 268–272.
Barkley et al., *Pediatrics*, 1990, 86(2), 184–192.
Barkley et al., *Pediatrics*, 1991, 87(4), 519–531.
Golinko, *Prog. Neuro–Psychopharm. Biol. Psychiat.*, 1984, 8, 1–8.

(List continued on next page.)

Primary Examiner—Thurman K. Page
Assistant Examiner—Humera N. Sheikh
(74) Attorney, Agent, or Firm—Woodcock Washburn LLP

(57) ABSTRACT

Dosage forms for oral administration of a methylphenidate drug are provided. The dosage forms provide a substantially immediate dose of methylphenidate upon ingestion, followed by one or more additional doses at predetermined times. By providing such a drug release profile, the dosage forms eliminate the need for a patient to carry an additional dose for ingestion during the day. The dosage forms and methods provided are useful in administering methylphenidate and pharmaceutically acceptable salts thereof, which generally require one or more doses throughout the day.

11 Claims, 2 Drawing Sheets

U.S. PATENT DOCUMENTS

| | | | |
|---|---|---|---|
| 4,968,505 A | 11/1990 | Okada et al. | 424/400 |
| 4,992,445 A | 2/1991 | Lawter et al. | 514/279 |
| 5,104,899 A | 4/1992 | Young et al. | 514/646 |
| 5,114,946 A | 5/1992 | Lawter et al. | 514/279 |
| 5,133,974 A | 7/1992 | Paradissis et al. | 424/480 |
| 5,156,850 A | 10/1992 | Wong et al. | 424/473 |
| 5,202,128 A | 4/1993 | Morella et al. | 424/469 |
| 5,217,718 A | 6/1993 | Colley et al. | 424/449 |
| 5,223,265 A | 6/1993 | Wong | 424/473 |
| 5,232,705 A | 8/1993 | Wong et al. | 424/473 |
| 5,283,193 A | 2/1994 | Yamamoto et al. | 435/280 |
| 5,284,769 A | 2/1994 | Evans et al. | 435/280 |
| 5,308,348 A | 5/1994 | Balaban et al. | 604/892.1 |
| 5,326,570 A | 7/1994 | Rudnic et al. | 424/458 |
| 5,331,000 A | 7/1994 | Young et al. | 514/570 |
| 5,362,755 A | 11/1994 | Barberich et al. | 514/649 |
| 5,375,693 A | 12/1994 | Woosley et al. | 514/317 |
| 5,449,743 A | 9/1995 | Kobayashi et al. | 528/355 |
| 5,478,573 A | 12/1995 | Eichel et al. | 424/480 |
| 5,500,227 A | 3/1996 | Oshlack et al. | 424/476 |
| 5,512,293 A | 4/1996 | Landrau et al. | 424/468 |
| 5,580,578 A | 12/1996 | Oshlack et al. | 424/468 |
| 5,593,694 A * | 1/1997 | Hayashida et al. | 424/468 |
| 5,639,476 A | 6/1997 | Oshlack et al. | 424/468 |
| 5,672,360 A | 9/1997 | Sackler et al. | 424/490 |
| 5,874,090 A | 2/1999 | Baker et al. | 424/400 |

FOREIGN PATENT DOCUMENTS

| | | |
|---|---|---|
| WO | WO 97/03672 | 2/1997 |
| WO | WO 97/03673 | 2/1997 |
| WO | WO 98/06380 | 2/1998 |
| WO | WO 98/14168 | 4/1998 |
| WO | WO 98/23263 | 6/1998 |
| WO | WO 99/62496 | 9/1999 |

OTHER PUBLICATIONS

Holmes et al., "Psychostimulant Response in Aids–Related Complex Patients", *J. Clin. Psychiatry,* 1989, 50(1), 5–8 (Biosis Abstract No. 87129969).

Srinivas et al., "Enantioselective Pharmacolinetics and Pharmacodynamics of Racemic Threo–Methylphenidate in Children with Attention Deficit Hyperactivity Disorder", *Clin. Pharmacol.,* 1992, 52(5), 561–568 (Biosis Abstract No. 95066168).

Aoyama et al., "Pharmacolinetics and pharmacodynamics of (+)–threo–methylphenidate enantiomer in patients with hypersomnia", *Clin. Phamacol. Ther.,* 1994, 55(3), 270–276.

Bowden et al., "Reactions of Carbonyl Compounds in Basic Solutions the Alkaline Hydrolysis of N–Methyl, N–Phenyl, and Bicyclo Lactams Penicillins, and N–Aklyl–N–methylacetamides", *J. Chem. Soc. Perkin Trans.,* 1990, 12, 2111–2116.

Brown, "Pharmacological Action and Drug Development", *Chirality in Drug Design and Synthesis,* Academic Press Inc., 1990, 4–7.

Brown G., "The Use of Methylphenidate for Cognitive Decline Associated with HIV Disease", *Int'l J. Psychiatry Med.,* 1995, 25(1), 21–37.

Corey et al., "A New Synthetic Approach to the Penicillins", *J. Am. Chem. Soc.,* 1965, 87(11), 2518–2519.

Ding et al., "Cis– and trans–Axetidin–2–ones from Nitrones and Copper Acetylide", *J. Chem. Soc. Perkin,* 1976, 22, 2382–2386.

Douzenis et al., "Phychiatric Disorder in HIV Disease: Description of 200 Referrals to a Liaison psychiatry Service", *Proc 7th. Int'l Conf. AIDS,* 1991, 215 (M.B.2135—Summary).

Earle et al., "Synthesis and Hydrolysis of some Fused–ring β–Lactams", *J. Chem. Soc.,* 1969, 2093–2098.

Greenhill L., "Attention–Deficit Hyperactivity Disorder", *Child & Adol. Psych. Clin. N.A.,* 1995, 4(1), 123–168.

Greenhill, "Pharmacologic Treatment of Attention Deficit Hyperactivity Disorder", *Pediatric Psychopharmacology,* 1992, 15(1), 1–27.

Hou, J.P. et al., "Beta–Lactam Antibiotics: Their Physicochemical Properties and Biological Activities in Relation to Structure", *J. Pharm. Sci.,* 1971, 60(4), 503–532.

Klibanov, "Asymmetric Transformations Catalyzed by Enzymes in Organic Solvents", *Acc. Chem. Res.,* 1990, 23, 114–120.

Moll R., "Darstellung von 1–Aza–bicyclo[4.2.0] octan–2–on", *Naturforsch Teil B.,* 1966, 21, 297.

Navia et al., "The AIDS Dementia Complex: I. Clinical Features", *Annals of Neurology,* 1986, 19, 517–524.

Patrick et al., "Pharmacology of the Enantiomers of threo–Methylphenidate", *J. Pharmacol & Exp. Terhap.,* 1987, 241, 152–158.

Rieder et al., "Diagnosis of Sulfonamide Hypersensitivity Reactions by In–Vitro "Rechallenge" with Hydroxylamine Metabolites", *Ann. Intern Med.,* 1989, 110, 286–289.

Scott, "Stereoisomers and Drug Toxicity", *Drug Safety,* 1993, 8(2), 149–159.

Srinivas et al., "Enantiomeric Gas Chromatography Assay with Electron Capture Detection for d–Ritalinic Acid in Plasma", *J. Chromatagraph,* 1990, 530, 327–336.

Srinivas et al., "Enantioselective Pharmacokinetics of dl–threo–Methylphenidate in Humans", *Pharmacol Res.,* 1993, 10(1), 14–21.

Srinivas et al., "Sterioselective Disposition of Methylphenidate in Children with Attention Deficit Disorder", *J. Pharmacol. Exp. Ther.,* 1987, 241(1), 300–306.

Uetrecht et al., "Idiosyncratic Drug Reactions: Possible Role of Reactive Metabolites Generated by Leukocytes", *Pharmacol Res.,* 1989, 6(4), 265–273.

White et al., "Methylphenidate as a Treatment for Depression in Acquired Immunodeficiency Syndrome: An n–of–1 Trial", *J. Clin. Psychiatry,* 1992, 53(5), 153–156.

Staal et al., "Glutathione deficiency and human immunodeficiency virus infection", *Lancet,* 1992, 339, 909–912.

Physician's Desk Reference, 46th ed., "Ritalin SR", 1992, 880–881.

* cited by examiner

DELIVERY OF MULTIPLE DOSES OF MEDICATIONS

CROSS-REFERENCE TO RELATED APPLICATIONS

This application is a divisional application of application Ser. No. 08/892,190, filed Jul, 14, 1997, now U.S. Pat. No. 5,837,284 which is a continuation in part of application Ser. No. 08/567,131, filed Dec. 4, 1995 now abandoned; application Ser. No. 08/583,317, filed Jan. 5, 1996 now U.S. Pat. No. 5,733,756; and application Ser. No. 08/647,642, filed May 15, 1996 now abandoned.

FIELD OF THE INVENTION

The present invention relates to improved dosing of medications. In particular, the present invention relates to improved dosing of a medication whereby two or more effective, time-separated doses may be provided by administration of a single dosage unit. The second, and any later, dose is time-delayed following administration. Based on predictable in vitro release times, the dosage forms can be formulated to deliver delayed doses in vivo at desired times.

The dosage forms and methods of the present invention are particularly suitable for the administration of methylphenidate hydrochloride, and especially for the administration of a single isomer, d-threo-methylphenidate hydrochloride.

The administration of dosage forms which contain an immediate dosage and a delayed second dosage provides for reduced abuse potential, improved convenience of administration, and better patient compliance, especially when methylphenidate is used to treat certain central nervous system disorders.

BACKGROUND OF THE INVENTION

Attention Deficit Disorder (ADD), a commonly diagnosed nervous system illness in children, is generally treated with methylphenidate hydrochloride (available commercially as, e.g., Ritalin®). Symptoms of ADD include distractibility and impulsivity. A related disorder, termed Attention Deficit Hyperactivity Disorder (ADHD), is further characterized by symptoms of hyperactivity, and is also treated with methylphenidate hydrochloride. Methylphenidate drugs have also been used to treat cognitive decline in patients with Acquired Immunodeficiency Syndrome (AIDS) or AIDS related conditions. See, e.g., Brown, G., *Intl. J. Psych. Med.* 25(1): 21–37 (1995); Holmes et al., *J. Clin. Psychiatry* 50: 5–8 (1989).

Methylphenidate exists as four separate optical isomers as follows:

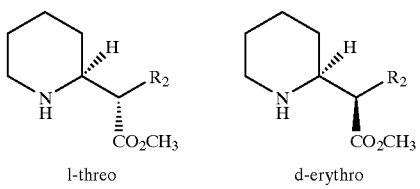

l-threo    d-erythro

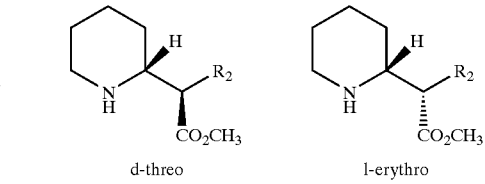

d-threo    l-erythro wherein $R_2$, is phenyl. Pharmaceutically acceptable salts are generally administered clinically. Other phenidate drugs, which also can be administered according to the invention, include those in which the methyl group in the above structures is replaced by $C_2$–$C_4$ alkyl and $R_2$ is optionally substituted with $C_1$–$C_4$ alkyl.

Clinically, the threo pair of enantiomers of methylphenidate hydrochloride is generally administered for the treatment of ADD and ADHD. The hydrochloride salt is commonly referred to simply as "methylphenidate". Unless indicated otherwise, the term "methylphenidate" is used broadly herein to include methylphenidate and pharmaceutically acceptable salts thereof, including methylphenidate hydrochloride.

The threo racemate (pair of enantiomers) of methylphenidate is a mild central nervous system stimulant with pharmacological activity qualitatively similar to that of amphetamines. Undesirable side effects associated with the use of the dl-threo racemate of methylphenidate include anorexia, weight loss, insomnia, dizziness and dysphoria. Furthermore, the racemate, which is a Schedule II controlled substance, produces a euphoric effect when administered intravenously or through inhalation or ingestion, and thus carries a high potential for abuse.

Srinivas et al. studied the administration of dl-threo-, d-threo, and l-threo-methylphenidate to children suffering from ADHD, and reported that the pharmacodynamic activity of dl-threo-methylphenidate resides in the d-threo isomer (*Clin. Pharmacol, Ther.*, 52: 561–568 (1992)). Therefore, while dl-threo-methylphenidate is generally used therapeutically, this racemate includes the l isomer which apparently makes no significant contribution to the pharmacological effectiveness of the drug, but likely contributes to the associated side effects. It is thus desirable to administer only the active d-threo form of the drug.

An additional problem is that children being treated with dl-threo methylphenidate must generally take one or more doses during the day. This creates a problem for school administrators who must store a controlled substance on school premises, with the associated risk that it may be stolen for illicit use. Furthermore, children may be traumatized by ridicule from peers when they must take medication at school.

Sustained release formulations of dl-threo methylphenidate have been developed, which provide for slow release of the drug over the course of the day. However, it has been observed that peak plasma concentrations of the drug are lower when sustained release formulations are used. In some studies, sustained release formulations of methylphenidate have been shown to have lower efficacy than conventional dosage forms.

There remains a need for methods for delivering methylphenidate with maximum effectiveness and minimal potential for abuse. Furthermore, it has been determined that there is a need for a dosage form which provides, in one administration, an initial release followed, at a predictable delay, by a second release, of maximally effective methylphenidate. This will eliminate the risk of theft or loss of the second dose, while minimizing undesirable side effects and maximizing ease of administration. The present invention is directed to these, as well as other, important ends.

SUMMARY OF THE INVENTION

Figure 1:
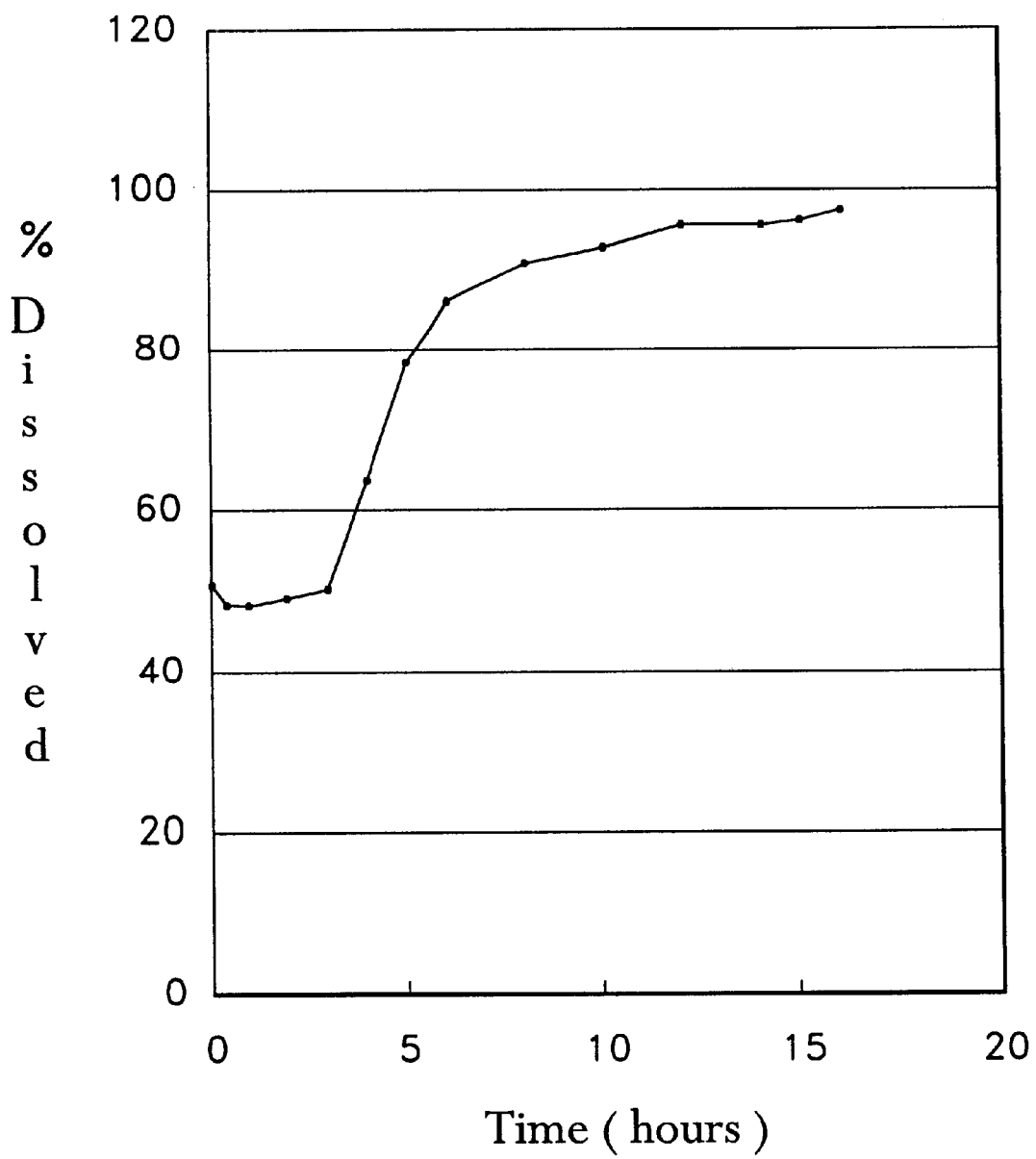
FIG. 1 depicts an in vitro time-concentration relationship (release profile) for certain preferred dosage forms in accordance with the invention.

The present invention provides, in one embodiment, a therapeutic composition for the oral administration of a methylphenidate drug comprising a dosage form containing two groups of particles, each containing the methylphenidate drug. The term "particles", as used herein, includes pellets, granules, and the like. The first group of particles provides a substantially immediate dose of the methylphenidate drug upon ingestion by a mammal. The first group of particles can also comprise a coating and/or sealant. The second group of particles comprises coated particles, which comprise from about 2% to about 75%, preferably from about 2.5% to about 50%, and more preferably from about 5% to about 20%, by weight of the second group of particles, of the methylphenidate drug, in admixture with one or more binders. The coating comprises a pharmaceutically acceptable ammonio methacrylate copolymer in an amount sufficient to provide a delay of from about 2 hours to about 7 hours following ingestion before release of the second dose. If desired, one or more additional doses may be delivered by additional particles, coated in a similar manner, but with a sufficient amount of ammonio methacrylate copolymer coating to provide the dosage after an additional delay. Methylphenidate and pharmaceutically acceptable salts thereof, including methylphenidate hydrochloride, can be prepared into the dosage forms of the invention.

In one embodiment of the present invention, the first group of particles comprises a methylphenidate drug and provides a substantially immediate dose of the methylphenidate drug upon ingestion by a mammal. The first group of particles may comprise a coating and/or sealant. The second group of particles comprises coated particles, which comprise from about 2% to about 75%, preferably from about 2.5% to about 50%, and more preferably from about 5% to about 20%, by weight of the particles of the methylphenidate drug in admixture with one or more binders. The coating comprises a pharmaceutically acceptable ammonio methacrylate copolymer in a quantity sufficient to provide a dose of methylphenidate delayed by from about 2 hours to about 7 hours following ingestion.

For example, the first group of particles can comprise a pharmaceutically acceptable salt of methylphenidate, such as methylphenidate hydrochloride, in powder form, or coated or uncoated particles containing the methylphenidate salt. The amount of methylphenidate salt in each group of particles can vary, depending upon the dosage requirements of the patient to whom the drug is to be administered. Generally, the daily dosage requirement for methylphenidate drugs is from about 1 mg to about 50 mg per day, preferably from about 2 mg to about 20 mg, and more preferably from about 2.5 to about 12 mg per day. The actual dosage to be administered will be determined by the attending physician as a matter of routine. Thus, depending upon the amounts of coating and/or and optional excipients and other additives, the amount of methylphenidate drug can be, for example, from about 2% to about 99% by weight of the first group of particles. In addition to the methylphenidate drug, the second group of particles comprises a filler, such as a hydrophobic filler, one or more ammonio methacrylate copolymers, and optional excipients and other additives. The filler can be present in an amount of, for example, from about 35% to about 45%, by weight, based on the total weight of the second group of particles.

Another embodiment of the present invention provides a method for treating disease, such as, for example, ADD, ADHD, or AIDS-related dementia, in a patient in need of treatment. This treatment comprises administering to the patient a dosage form providing once-daily oral administration of a methylphenidate drug such as methylphenidate hydrochloride. The dosage form comprises at least two groups of particles, each containing the methylphenidate drug. The first group of particles comprises from about 2% to about 99% by weight of the methylphenidate drug, depending upon desired the daily dosage, and provides a substantially immediate dose of methylphenidate upon ingestion by a mammal. The first group may comprise a coating and/or sealant. The second group of particles comprises coated particles. The coated particles comprise the methylphenidate drug in admixture with one or more binders, wherein the amount of methylphenidate drug is from about 2% to about 75%, preferably from about 2.5% to about 50%, and more preferably from about 5% to about 20%, by weight of the second group of particles, and a coating comprising an ammonio methacrylate copolymer in a quantity sufficient to provide a dose of methylphenidate delayed by from about 2 hours to about 7 hours following ingestion. The components of the two groups of particles can vary as described hereinabove. The initial dose can be administered separately from the delayed dose, if desired.

A further embodiment of the present invention provides dosage forms for the oral administration, in a single dosage form, of two doses of a pharmaceutically acceptable salt of d-threo-methylphenidate. The dosage forms comprise particles containing within their interiors from about 2% to about 75%, preferably from about 2.5% to about 50%, and more preferably from about 5% to about 20%, of the d-threo-methylphenidate salt, in admixture with one or more binders. The particles have a coating exterior to the methylphenidate salt, which comprises an ammonio methacrylate copolymer in a quantity sufficient to delay release of the d-threo-methylphenidate salt contained within by from about 2 hours to about 7 hours following administration. The dosage forms also comprise, exterior to the coating, an outer layer comprising from about 2% to about 99% by weight of the d-threo-methylphenidate salt, based on the weight of all components in the outer layer, to provide a substantially immediate dose of the d-threo-methylphenidate salt upon administration. The layer comprising the immediate dose of the d-threo-methylphenidate salt can, if desired, further comprise an outer sealant layer. If desired, the two doses of the d-threo-methylphenidate salt can be approximately equal.

The present invention also provides dosage forms providing plasma concentration profiles for methylphenidate having two maxima, temporally separated from each other by from about 2 hours to about 7 hours. Preferably, the magnitude of said maxima differs by no more than about 30 percent, more preferably by no more than about 20 percent, and most preferably by no more than about 10 percent.

"Methylphenidate" as used herein, includes all four optical isomers of the compound and all pharmaceutically acceptable salts thereof. When one or more particular isomers is contemplated, the isomer is indicated, as in d-threo, l-threo, etc. The combined threo isomers may be indicated simply as "threo" and the erythro isomers as "erythro". For therapeutic use in treating conditions treatable by methylphenidate drugs, dl-threo methylphenidate hydrochloride is generally used, while d-threo methylphenidate hydrochloride is preferred according to the present invention.

As discussed, the four isomers have exhibited varying levels of therapeutic activity, and have been shown to differ generally in producing unwanted side effects. The present invention provides dosage forms which maximize therapeutic effectiveness and minimize undesirable side effects. In certain preferred embodiments, the dosage forms of the present invention provide administration of the two threo forms of methylphenidate. In particularly preferred embodiments, the dosage forms of the present invention provide administration of a single isomer, d-threo-methylphenidate, albeit in two or more doses.

The dosage forms of the present invention are intended for oral ingestion by a mammal, particularly a human. The dosage forms of the present invention are particularly suitable for the administration of methylphenidate drugs, in at least two doses. Most preferably, the dosage forms provide two doses of a d-threo methylphenidate drug such as d-threo methylphenidate hydrochloride. The second dose can be delayed by from about 2 hours to about 7 hours, preferably from about 3 hours to about 6 hours, and most preferably from about 4 hours to about 5 hours, following ingestion of the dosage form by a mammal. This eliminates the need for a patient, for example a child being treated for ADD, to carry a second dose for ingestion several hours after ingestion of a first dose. The exclusion of the l isomers and the d-erythro isomer eliminates the concurrent ingestion of forms of methylphenidate principally believed to be associated with adverse side effects and/or reduced effectiveness.

The temporal separation of the two doses provided according to the present invention can be represented graphically as in FIG. 1. FIG. 1 is an in vitro drug release profile of a dosage form of the present invention. The data were obtained by measuring the rate of dissolution of drug as a function of time. In this embodiment two doses are provided. The release of the first dose preferably occurs substantially immediately; for example, within about 30 minutes following administration. Following a period of little or substantially no drug release, the second dose is released. The two releases can be referred to as "pulses", and such a release profile can be referred to as "pulsatile".

Figure 2:
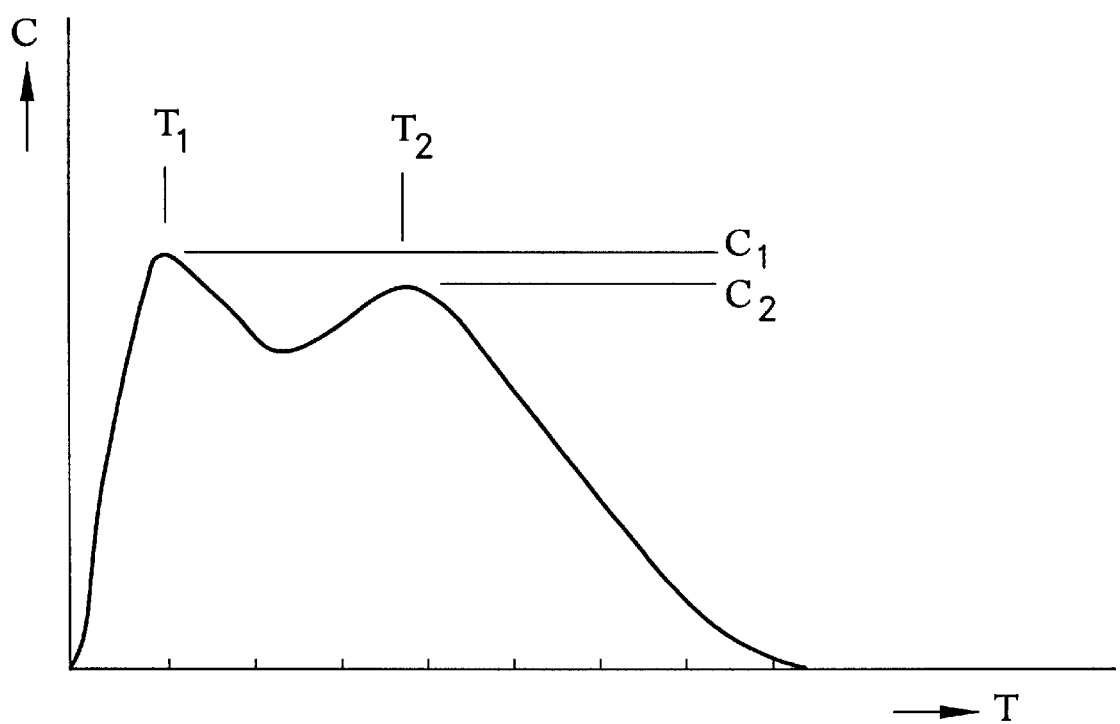
FIG. 2 depicts a schematic representation of in vivo plasma concentration of a drug released according to the release profile shown in FIG. 1.

FIG. 2 is a schematic representation of the plasma concentration of drug resulting from a release profile according to FIG. 1. The maximum concentration due to the first dose, $C_1$, occurs at $t_1$, preferably from about 1 hour to about 3 hours after ingestion, most preferably about 2 hours after ingestion. The release of the first dose is followed by a period during which substantially no drug is released, which lasts approximately 2–6 hours, preferably 3–5 hours, post ingestion. The second dose is then released, with the maximum concentration, $C_2$, at $t_2$, which is preferably about 6 hours post-ingestion. Preferably at least about 80% of the total drug has been released by about 6 hours following administration. In the embodiment represented by FIG. 2, the levels of drug released at the two maxima are nearly equal. Preferably, if two approximately equal doses are released, the release of the two doses provides a plasma concentration profile having two maxima, which differ from each other by no more than about 40 percent in magnitude, preferably by no more than about 30 percent, and more preferably by no more than about 25 percent. This is determined by the relationship:

$$|C_1-C_2|/C_1$$

In such embodiments is most preferred that the maxima differ by no more than 20%. However, embodiments in which the maxima of the two releases differ by more than 40 percent are within the scope of the invention. The appropriate relative amounts of drug in each release can be readily determined by one skilled in the art.

Dosage forms of the present invention provide controlled release of a methylphenidate drug, including pharmaceutically acceptable salts of methylphenidate, whereby an initial dose for immediate release can be combined with a delayed release of one or more additional doses. Such dosage forms may alternatively be referred to as "pulsatile" dosage forms.

"Immediate release", as used herein, means release within about a half hour following ingestion, preferably about 15 minutes, and more preferably within about 5 minutes following ingestion. "Delayed release", as used herein, refers to a drug release profile which includes a period during which no more than about 10 percent of the drug in a particular dosage form is released, followed by a period of from about 0.5 hour to about 2.5 hours, preferably about 1.5 hours, more preferably about 1 hour, in which no less than about 70 percent, preferably no less than about 80 percent, and more preferably no less than about 90 percent, of the drug is released. The terms "medication" and "drug" are used interchangeably herein.

According to the present invention, delayed release dosage forms can be combined with forms which provide immediate release of a drug. Thus, two or more dosage forms can be combined, one dosage form providing a portion of a patient's daily dosage needs of a drug and subsequent dosage forms providing additional portions of a patient's daily dosage needs. For example, a drug can be administered to a patient in two dosage forms simultaneously, one providing, e.g., about 30–50 percent of the patient's daily requirement of the drug and the second providing the remainder of the patient's daily requirement. Alternatively, and preferably, a single dosage form can be administered which includes an immediate dose of some portion of a patient's daily requirement and one or more delayed doses to provide the remaining portion or portions of the patient's daily requirement.

Dosage forms of the present invention provide an initial dose of a drug such as, for example, a pharmaceutically acceptable salt of d-threo-methylphenidate (also referred to herein as d-MPD), followed by an interval wherein substantially no additional drug is released, followed in turn by release of a second dose. If desired, a second substantially release-free interval may be provided following the second release, followed in turn by a third dose. Thus, dosage forms providing 3 or more doses are contemplated by the present invention. However, dosage forms providing 2 or 3 doses are generally preferred for therapeutic use, with 2 doses being more preferred. For example, the first dose can provide from about 30 percent to about 70 percent of a patient's daily prescribed intake of the drug and the second dose provides from about 70 percent to about 30 percent. If two approximately equal doses are desired, the initial dose preferably provides from about 40 percent to about 60 percent, and the second dose preferably provides from about 60 percent to about 40 percent, of a patient's prescribed daily intake of the drug. If desired, the first dose and the second dose can each provide about 50 percent of a patient's prescribed daily intake of drug. However, as will be apparent to one skilled in the art, the effect of drug metabolism in the body may require adjustment of the relative amounts of each dose, so that, for example, the second dose may have to be adjusted to provide more of the drug than the first dose, to compensate for any competition between drug release and drug metabolism. This can be observed in FIG. 2, which, as discussed above, represents the blood plasma level of a drug, such as a methylphenidate drug, delivered in a dosage form which provides a release profile as illustrated in FIG. 1.

The initial dose of methylphenidate drug in the dosage forms of the present invention can be provided by incorporating the methylphenidate drug into a form which allows for substantially immediate release of the drug once the dosage form is ingested by a patient. Such forms include, for example, powders, coated and uncoated pellets, and coated and uncoated tablets. The dose for immediate release can be administered in a tablet or capsule form which may also include the delayed dose. For example, two or more groups of pellets may be combined within a hard gelatin capsule or compressed into a tablet. Powders can be granulated and can be combined with pellets and excipients and/or other additives, and contained within a capsule or compressed into a tablet. These and other dosage forms will be familiar to those skilled in the art.

The delayed dose of a methylphenidate drug in the dosage forms of the present invention is provided in part by the use of certain copolymers referred to as "ammonio methacrylate copolymers". Ammonio methacrylate copolymers comprise acrylic and/or methacrylic ester groups together with quaternary ammonium groups. According to the present invention, the copolymers are incorporated into a formulation which is used to coat particles containing a medication.

The "acrylic and/or methacrylic ester groups" in the copolymers used in the compositions and methods of the present invention are referred to herein collectively as "acrylic groups". The acrylic groups are preferably derived from monomers selected from $C_1$–$C_6$ alkyl esters of acrylic acid and $C_1$–$C_6$ alkyl esters of methacrylic acid. Preferred are $C_1$–$C_4$ alkyl esters of acrylic acid and methacrylic acid. Suitable monomers include, for example, methyl acrylate, ethyl acrylate, methyl methacrylate, and ethyl methacrylate. Ethyl acrylate and methyl methacrylate are preferred, and copolymers containing ethyl acrylate and methyl methacrylate are highly preferred. Also preferably, the copolymers have a molecular weight of about 150,000.

Quaternary ammonium groups in copolymers useful in forming coatings for use in the dosage forms of the present invention can be derived from monomers comprising quaternary ammonium groups. Preferably, the monomers are alkyl esters of acrylic or methacrylic acid, comprising alkyl groups having from 1 to 6 carbon atoms and a quaternary ammonium group in the alkyl portion. Monomers comprising quaternary ammonium groups can be prepared, for example, by reaction of monomers containing amino groups with alkylating agents such as, for example, alkyl halides, especially methyl chloride. Suitable monomers containing amino groups include 2-(N,N-dibutylamino) ethyl acrylate, 2-(N,N-dibutylamino) ethyl methacrylate, 4-diethylamino-1-methyl-butyl acrylamide, and 4-diethylamino-1-methylbutyl methacrylamide. Other useful monomers containing amino groups are disclosed in U.S. Pat. No. 5,422,121, the disclosure of which is incorporated herein by reference. Particularly preferred as a monomer comprising a quaternary ammonium group is trimethylammonioethyl methacrylate chloride (TAMCl).

While ammonio methacrylate copolymers such as those described herein have been used for sustained delivery of certain medicaments, i.e., for the relatively constant administration of a drug, it has been surprisingly and unexpectedly found that dosage forms comprising a methylphenidate drug and a coating prepared from one or more ammonio methacrylate copolymers and certain fillers, can provide delayed or pulsatile release of the drug, a very distinct phenomenon. Methylphenidate drugs are amine-containing, rely upon body or membrane loading for efficacy, and are psychotropic. The ability to provide delayed release of a methylphenidate drugs using ammonio methacrylate copolymers is due to a combination of factors, including the composition of the ammonio methacrylate copolymers used, and the amount and composition of filler.

The ratio of acrylic groups to quaternary ammonium groups in the ammonio methacrylate copolymers influences the properties of the copolymers utilized in forming the coatings of the present invention. For use in the dosage forms and methods of the present invention, the ratio of acrylic groups to quaternary ammonium groups in the copolymers is preferably from about 10:1 to about 50:1, more preferably from about 15:1 to about 45:1. Preferably, in preparing a dosage form according to the present invention, two or more copolymers are used in combination. Also preferably, one of the copolymers comprises acrylic groups and quaternary ammonium groups in a ratio of from about 25:1 to about 45:1, more preferably from about 30:1 to about 40:1, and another of the copolymers comprises acrylic groups and quaternary ammonium groups in a ratio of from about 10:1 to about 25:1, more preferably from about 15:1 to about 20:1. Even more preferably, two ammonio methacrylate copolymers are used: a first copolymer comprising acrylic groups and quaternary ammonium groups in a ratio of from about 30:1 to about 40:1 and the second copolymer comprising acrylic groups and quaternary ammonium groups in a ratio of from about 15:1 to about 20:1. Most preferably, the copolymers are copolymers of methyl methacrylate, ethyl acrylate, and TAMCl, in ratios of 2:1:0.1 for the first copolymer and 2:1:0.2 for the second copolymer.

When two such ammonio methacrylate copolymers are used to form the coatings, the relative amounts of the two polymers is partly determinative of the delay and release properties of the dosage forms of the present invention. It is preferred that the ratio between the first polymer, most preferably having an acrylic group/quaternary ammonium group ratio of from about 30:1 to about 40:1, and the second polymer, most preferably having an acrylic group/quaternary ammonium group ratio of from about 15:1 to about 20:1, be from about 93:7 to about 97:3. More preferably, the ratio of the first polymer to the second polymer is from about 96:4 to about 94:6, and most preferably about 95:5.

Ammonio methacrylate copolymers used in the coatings of the dosage forms of the present invention can be prepared by methods known to those skilled in the art. Exemplary methods include emulsion polymerization, bulk polymerization and suspension polymerization. A suitable procedure is described in U.S. Pat. No. 3,979,349, the disclosure of which is incorporated herein by reference. Suitable ammonio methacrylate copolymers are known per se, and can be purchased from commercial providers. For example, suitable ammonio methacrylate polymers are available from Hüils America under the Eudragit® trademarks. The Eudragit® polymers and similar polymers, including methods for preparation, are described in Klaus O. R. Lehman, "Chemistry and Application Properties of Polymethacrylate Coating Systems", *Aqueous Polymeric Coatings for Pharmaceutical Dosage*

*Forms,* 2nd. Ed., pp. 101–174, James Mc Ginity, Ed., Marcel Dekker, Inc., N.Y. (1996), the disclosure of which is incorporated herein by reference.

The coatings of the present invention also preferably include a filler. The filler is preferably in powder form and is preferably hydrophobic. Exemplary fillers include talc, colloidal silica, fumed silica, gypsum, and glycerine monostearate. Talc is a particularly preferred filler.

The quantity of filler used in preparing coatings for the dosage forms of the present invention should be sufficient to minimize agglomeration of the particles. Agglomeration is highly undesirable because the agglomerates, rather than discrete particles, will become coated. Agglomerates are susceptible to breaking into discrete particles, which will be partially uncoated, resulting in unwanted variability in release rates. Preferably, the amount of filler is from about 30 percent to about 50 percent by weight, based on the total weight of the dry polymer, commonly referred to as "total solids". More preferably the amount of filler is from about 35 percent to about 45 percent of total solids, and most preferably about 40 percent.

Coatings used in the dosage forms of the present invention also preferably include a material which improves the processing of the copolymers. Such materials are generally referred to as "plasticizers" and include, for example, citric acid esters, adipates, azelates, benzoates, citrates, stearates, isobucates, sebacates, propanetriol acetate, polyethylene glycols, diethyl phthalate, dibutyl sebacate, propylene glycol and ethylene glycol. Citric acid esters are preferred, and triethyl citrate is particularly preferred. The amount of plasticizer to be used in the coating is preferably from about 10 percent to about 30 percent, more preferably from about 15 percent to about 25 percent, and most preferably about 20 percent, based on the weight of the dry polymer, i.e., total solids.

Dosage forms of the present invention preferably comprise particles containing d-MPD. In one embodiment, the dosage form comprises two groups of particles. A first group of particles provides the initial dose of d-MPD. As stated hereinabove, the initial dose can be in powder, pellet or other particulate form and can be uncoated. If the initial dose is in the form of a powder or sufficiently small particles, it can, if desired, be pressed into a solid form such as a tablet or caplet. In this embodiment, the delayed dose is provided by a second group of particles. The second group of particles is preferably in the form of pellets. The pellets can be of any shape, such as, for example, spheroids or ellipsoids, or may be irregularly shaped.

Suitable pellets for the initial dose and/or the second dose can be formed by, for example, depositing a layer of drug, and optional excipients, carriers, and other optional materials, onto small, pharmaceutically acceptable particles such as nonpareils. Such a layer can be deposited by methods known to those skilled in the art, such as, for example, spraying, using methods and equipment known to those skilled in the art. For example, a Wurster air suspension coater can be used. Spraying can also be accomplished using a pan coating system, wherein the drug is deposited by successive spraying accompanied by tumbling in a rotating pan. Alternatively, pellets can be formed, for either or both of the initial and delayed dose, by extrusion of the drug with suitable plasticizers and other processing aids as necessary.

Tablets or caplets, or other solid dose forms, comprising the initial dose and/or delayed dose or doses, can conveniently be administered. A solid dose form can be prepared by methods known to those skilled in the art. For example, the d-MPD, filler and other optional components may be compressed into tablets or inserted into capsules. If desired, the drug and other components of the dose form can be granulated, using processing aids, fillers, aqueous or non-aqueous solvents, and binders known to those skilled in the art. Granules can be filled into capsules, if desired. Alternatively, the d-MPD can be blended with a solvent and processed by known methods such as ball-milling, calendering, stirring, or roll-milling, then pressed into a desired shape. Suitable solvents useful in forming the particles comprising d-MPD, and other components of the dosage forms of the invention, include inert organic and inorganic solvents which do not adversely affect the components of the dosage forms. While water can be used for many drugs, including methylphenidate, useful solvents can be selected from the group consisting of aqueous solvents, alcohols, ketones, esters, ethers, aliphatic hydrocarbons, halogenated solvents, cycloaliphatics, aromatic heterocyclic solvents, and mixtures thereof. Other solvents include acetone, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, nitroethane, nitropropane, tetrachloroethane, diglyme, and aqueous and non-aqueous mixtures thereof, such as acetone and water, acetone and methanol, acetone and ethyl alcohol, and ethylene dichloride and methanol.

Following the formation of suitable particles, those particles to be used to deliver the delayed dose are then coated with a polymer-containing coating as described herein. The amount of coating to be used in forming the dosage forms, particularly the delayed dose, of the present invention, will be determined by the desired delivery properties, including the amount of drug to be delivered, the delay time required, and the size of the particles. Preferably, the coating on the particles providing the delayed dose, including all solid components of the coating such as copolymer, filler, plasticizer and optional additives and processing aids, is from about 10 percent to about 60 percent, more preferably from about 20 percent to about 50 percent, most preferably from about 30 percent to about 40 percent, of the total final weight of the particles. The appropriate amount of coating can advantageously be determined using in vitro measurements of drug release rates obtained with selected amounts of coating. The coating can be deposited by any method known to those skilled in the art, such as spray application. Spraying can be carried out by pan coating or by use of a fluid bed, such as the Wurster fluid bed described for use in depositing a drug.

After deposition of the drug, a sealant can be applied to any and/or all of the particles, prior to application of the polymeric coating. A sealant provides a physical barrier between the drug and the coating, to minimize or prevent interaction between the drug and the coating. Suitable sealants can be prepared from materials such as biologically inert, permeable, pharmaceutically acceptable polymers, such as, for example, hydroxypropylalkylcelluloses, wherein "alkyl" refers to $C_1$–$C_6$ hydrocarbon chains. Exemplary materials include hydroxypropyl methylcellulose, hydroxypropylethylcellulose, hydroxypropyl propylcellulose, and hydroxypropylbutylcellulose. Hydroxypropylmethylcellulose is preferred. While other materials are known to those skilled in the art for use as sealants, such as, for example, cellulose acetate methyl carbamate, cellulose acetate diethyl aminoacetate, semipermeable polyurethanes, semipermeable sulfonated polystyrenes, semipermeable cross-linked polymers such as poly(vinylbenzyltrimethyl)ammonium chloride, these are not preferred as they may affect the release rate of certain drugs including d-MPD. A sealant can be prepared by adding the material to water, and agitating for a time and at a rate sufficient to form a solution. The formation of a solution will be indicated, for example, by transparency and the absence of visually observable suspended material. The amount of material added to the water is not critical but is determined by viscosity. A solution which is too viscous will present difficulties in spraying. Generally, the amount of material should not exceed about 20 weight/volume percent, i.e., 20 g sealant material per 100 ml of water. Preferably, the amount of material in the water is from about 5 percent to about 15 weight/volume percent, and more preferably about 10 weight/volume percent.

Following deposition of the optional sealant and the coating, the coated particles are cured. "Curing" means that the particles are held at a controlled temperature for a time sufficient to provide stable release rates. Stability in release rate is indicated when further curing does not affect the release rate. In contrast, instability of release rate means that as the cure time is increased, the release rate continues to vary. Curing for a sufficient time ensures that substantially the same release rate is obtained with all particles of a particular size coated with a given amount of a given coating composition. A suitable curing time can be determined by one of skill in the art without undue experimentation, by noting the variability in in vitro release times as curing time is varied. As a general guideline, many formulations can be cured in about 24 hours.

Curing can be accomplished, for example, in a forced air oven. Curing can be carried out at any temperature above room temperature, "room temperature" being defined as from about 18° C. to about 25° C. Preferably, curing is carried out at a temperature of from about 30° C. to about 50° C., more preferably from about 35° C. to about 45° C., and most preferably about 40° C. Curing time can range from several hours to several days. Preferably, the coated particles are cured for at least about 24 hours, more preferably at least about 2 days, even more preferably at least about 3 days, still more preferably at least about 4 days, still even more preferably at least about 5 days, even more preferably at least about 6 days, and most preferably for about 7 days. While no significant adverse effects or advantages have been observed when the particles are cured for longer than about 7 days, it has been found that curing for less than about 24 hours may result in relatively poorer storage stability as compared to particles cured for longer periods of time.

The amount of methylphenidate drug contained in the first and second groups of particles depends upon the prescribed dosage to be delivered to a patient. The first group of particles can consist substantially entirely of a methylphenidate drug. "Substantially entirely" means that about 95 percent or more of the weight of the first group of particles can consist of a methylphenidate drug. If desired, the first group of particles can also contain pharmaceutically acceptable carriers, excipients, and other components which do not interfere with the substantially immediate release of the medication. "Substantially immediate" release, as used herein, means that at least about 90 percent of the medication is released within about 30 minutes from the time the drug is ingested. The second group of particles can contain from about 2 percent to about 75 percent, preferably from about 4 percent to about 50 percent, medication, based on the total weight of the particles including the coating to be deposited thereon.

According to the invention, a first and a second group of particles can be administered simultaneously as part of one dosage form. Any dosage form can be used. For example, the two groups of particles can be combined within a capsule. Alternatively, the two groups of particles can be pressed into a solid form such as a tablet. In pressing the particles into a solid form, suitable processing aids known to those skilled in the art can be used. Alternatively, particles coated to provide a delayed dose of a medication can be dispersed within or blended with, the medication in powder form.

As discussed, the dosage form can comprise a single group of particles providing both a substantially immediate dose of a methylphenidate drug, and a delayed dose of methylphenidate drug. The particles comprise, in admixture with one or more binders, from about 2% to about 75% by weight of a methylphenidate drug for delayed release, and a coating comprising the pharmaceutically acceptable, substantially neutral copolymers described herein. The particles further comprise, exterior to the coating, an outer layer comprising methylphenidate drug, to provide an initial, substantially immediate, dose. The substantially immediate dose is preferably released within about 30 minutes, more preferably about 15 minutes, and most preferably within about 5 minutes following ingestion. The outer layer can optionally comprise additives such as, for example, binders, excipients, and lubricants known to those skilled in the art.

The dosage forms provided by the invention can be of any shape suitable for oral administration of a drug, such as spheroidal, cube-shaped, oval, bean shaped, or ellipsoidal. The dosage form may be in the form of granules, which may be irregularly shaped. In any of the embodiments of the present invention, although the size of the particles is generally not critical, a certain particle size or sizes can be preferred depending upon the characteristics of the dosage form. For example, the dosage form can comprise a capsule containing a first and/or second group of particles. The particles should then be of a size which allows for ease in handling, and which allows for the particles comprising a desired quantity of drug to be readily measured and inserted into the capsule. If the dosage form comprises a single group of particles providing a substantially immediate dose and a delayed dose, the particles are preferably of a size and shape which facilitate oral administration. For example, the particles can be in the form of tablets, caplets, etc. Alternatively, the particles can be contained within a capsule of suitable size and shape for oral administration. If desired, various fillers and/or binders known to those skilled in the art can be included in the particles to provide the desired size and shape.

It will be recognized by one skilled in the art that the dosage forms of the present invention may include, in either or both of the first dose and any delayed dose, pharmaceutically acceptable carriers, extenders, fillers, processing aids, and excipients known to those skilled in the art.

The following examples are merely illustrative of the present invention and should not be considered limiting of the scope of the invention in any way. These examples and equivalents thereof will become more apparent to those skilled in the art in light of the present disclosure and the accompanying claims.

EXAMPLE 1

Preparation of Layered Pellets Containing d-MPD Hydrochloride

A solution of d-MPD hydrochloride was prepared as follows. To 300 grams (g) of deionized water were added 100 g of d-MPD hydrochloride, followed by moderate mixing, using a stirring paddle, for 5 minutes. A 10 percent (weight) solution of hydroxypropyl methylcellulose (HPMC E-6 from Dow Chemicals, Midland, Mich.; 250 g) was added, followed by homogenization for 5 minutes using an emulsifier head (Silverson, Chesham, UK; Model L4R). After addition of another 150 g of deionized water, the solution was sonicated for 15 minutes (Sonicor Model SC-150T; Instruments Corporation, Copiague, N.Y.), at which time the solution was clear.

A second solution was prepared by combining 300 g of deionized water and 300 g of a 10% (wt) HPMC E-6 solution and mixing for 5 minutes.

The first solution was sprayed onto 25/30 mesh non-pareil seeds (Ozone Co., Elmwood Park, N.J.) in a fluid bed apparatus (GPCG-1, Glatt Air Techniques, Inc., Ramsey, N.J.) using a Wurster head. The second solution was then sprayed to form a sealant. For both solutions, the spray rate was 8–9 g/minute. Inlet temperature was 50–55° C. and the non-pareil seeds were maintained at 35–40° C. Air volume was 6–7 meters per second (m/s).

EXAMPLE 2
Preparation of Coated Pellets Containing d-MPD Hydrochloride

A dispersion of 844 g of Eudragit® RS30D (ammoniomethacrylate copolymer from Hüls America, Somerset, N.J.; EA/MMA/TAMCI 1:2:0.1), was screened through a 60 mesh screen, then stirred for 15 minutes. A dispersion of 44 g of Eudragit® RL30D (EA/MMA/TAMCl 1:2:0.2) was similarly screened and stirred. The two dispersions were combined and stirred for 15 minutes, forming a combined dispersion. Triethyl citrate (TEC; from Moreflex, Greensboro, N.C.; 54 g) was added, followed by an additional 15 minutes of stirring. Deionized water (664 g) was added, followed by 15 minutes of stirring. Talc (108 g; from Luzenac, Englewood, Colo.) was added, followed by further stirring for 15 minutes.

The resulting combined dispersion was sprayed onto layered pellets prepared according to Example 1, using a fluid bed apparatus as used in Example 1. Spray rate was 9–10 g/minute, inlet temperature 40–45° C., and air volume 5–6 m/s. The non-pareils were maintained at 30–35° C. during spraying. A total of 960 g of dispersion was sprayed onto the pellets, representing a 30% weight increase due to the applied coating.

EXAMPLE 3
Evaluation of Drug Release Profile for Coated Pellets Prepared According to Example 2

Pellets were prepared according to Example 2, varying the ratios of the polymers between 90:10 and 93:7.
Dissolution Measurements Dissolution was carried out in order to determine rate of release of d-MPD from the pellets. USP Apparatus I (United States Pharmacoepia Convention, Rockville, Md.) was used. The dissolution medium was 900 ml of deionized water (unless otherwise specified) and the temperature was maintained at 37° C. The sample cell size was 1 cm (a flow through cell), and the samples were stirred continuously at 100 rpm. The apparatus was equipped with a diode array spectrophotometer, and absorption at 220 nanometers (nanometers (nm)) was measured to determine the concentration of d-MPD. Samples were measured at 60, 120, 180, 240, 360, 480, 600, 720, 840, 900, 960, 1080, 1200, 1320 and 1440 minutes.

Results of the dissolution measurements are presented in Table 1. The results indicate that the amount of drug released is influenced by: amount of coating, ratio of the two polymers, amount of talc, and curing time.

EXAMPLE 4: COMPARATIVE EXAMPLE

A dispersion of 911.25 g of Eudragit® RS30D was passed through a 60 mesh screen and mixed with a similarly screened dispersion of 101.25 g of Eudragit® RL30D for 15 minutes at moderate speed. Triethyl citrate (61 g) was added, followed by an additional 15 minutes of mixing. After mixing, 991.5 g of deionized water, then 61 g of talc were added with 15 additional minutes of mixing following each addition. The resulting dispersion (1600 g) was sprayed onto 800 g of layered sealed pellets prepared according to Example 1.

No delay was observed; substantially all of the drug was released within approximately one hour. Result is shown in Table 1 (Trial 1).

EXAMPLE 5: COMPARATIVE EXAMPLE

A dispersion of 600 g of Eudragit® NE30D was screened through a 60 mesh screen and mixed with a 600 g dispersion of magnesium stearate for 15 minutes at moderate speed. The resulting dispersion (750 g) was sprayed onto 750 g of layered and sealed pellets prepared according to Example 1.

After a delay of 2 hours, release of the drug was observed. About 85% of the drug was released after 14 total hours.

TABLE 1

RELEASE TIMES

| Trial No. | % coat | Ratio | Delay | Talc, % | Cure time | Time for 85% release |
|---|---|---|---|---|---|---|
| 1 | 40 | 90:10 | none | 20.0 | 24 hrs | 1.0 |
| 2 | 30 | 95:5 | 4.0 | 20.0 | " | 8.0 |
| 3 | 30 | 95:5 | 4.0 | 20.0 | " | 8.0 |
| 4 | 30 | 93:7 | 1.0 | 20.0 | " | 3.0 |
| 5 | 40 | 93:7 | 1.0 | 20.0 | " | 4.0 |
| 6 | 30 | 93.5:6.5 | 2.0 | 20.0 | " | 5.0 |
| 7 | 40 | " | 2.0 | 20.0 | " | 5.0 |
| 8 | 30 | 94.5:5.5 | 2.0 | 20.0 | " | 8.0 |
| 9 | 40 | " | 1.0 | 20.0 | " | 5.0 |
| 10 | 30 | 94:6 | 2.0 | 20.0 | " | 5.0 |
| 11 | 40 | " | 2.0 | 20.0 | " | 5.0 |
| 12 | 30 | 95:5 | 2.0 | 40.0 | " | 5.0 |
| 13 | 40 | " | 3.0 | 40.0 | " | 8.0 |
| 14 | 30 | 96:4 | 4.0 | 40.0 | " | 10.0 |
| 15 | 40 | " | 5.0 | 40.0 | " | 10.0 |
| 16 | 30 | " | 4.0 | 40.0 | 7 days | 10.0 |
| 17 | 20 | 95:5 | 2.0 | 40.0 | " | 5.0 |
| 18 | 30 | " | 3.0 | 40.0 | " | 6.0 |
| 19 | 30 | " | 3.0 | 40.0 | " | 6.0 |
| 20 | 30 | " | 2.0 | 40.0 | " | 6.0 |
| 21 | 40 | " | 3.0 | 40.0 | " | 8.0 |

What is claimed is:

1. A method for treating disease amenable to treatment with a phenidate drug in a patient in need of such treatment comprising administering to the patient a dosage form providing once-daily oral administration of d-threo-methylphenidate hydrochloride, said dosage form comprising two groups of particles, each containing d-threo-methylphenidate, wherein:
   a) said first group of particles comprises from about 2% to about 99% by weight of d-threo-methylphenidate hydrochloride and provides a substantially immediate dose of said d-threo methylphenidate upon ingestion by a mammal; and
   b) said second group of particles comprises coated particles, said coated particles comprising from about 2% to about 75% by weight of d-threo-methylphenidate in admixture with one or more binders, and a coating consisting of an ammonio methacrylate copolymer in an amount sufficient to provide a dose of said d-threo-methylphenidate hydrochloride delayed by from about 2 hours to about 7 hours following said ingestion.

2. A dosage form of a pharmaceutically acceptable salt of a methylphenidate providing an in vivo plasma concentration of said methylphenidate comprising two maxima, wherein said maxima are temporally separated by from about two hours to about seven hours and wherein the magnitude of said maxima differ by no more than about 30%.

3. A method for treating disease amenable to treatment with a phenidate drug in a patient in need of such treatment comprising administering to the patient a dosage form providing once-daily oral administration of the phenidate drug, said dosage form comprising two groups of particles, each containing the drug wherein:

a) said first group of particles comprises from about 2% to about 99% by weight of the phenidate drug and provides a substantially immediate dose of said phenidate drug upon ingestion by a mammal; and b) said second group of particles comprises coated particles, said coated particles comprising from about 2% to about 75% by weight of the phenidate drug in admixture with one or more binders, and a coating consisting of an ammonio methacrylate copolymer in an amount sufficient to provide a dose of said phenidate drug delayed by from about 2 hours to about 7 hours following said ingestion.

4. The method of claim 3 wherein said delay is at least about 3 hours.

5. The method of claim 3 wherein said delay is at least about 4 hours.

6. The method of claim 1 wherein said delay is at least about 3 hours.

7. The method of claim 1 wherein said delay is at least about 4 hours.

8. The dosage form of claim 2 wherein the temporal separation is at least about 3 hours.

9. The dosage form of claim 2 wherein the temporal separation is at least about 4 hours.

10. A method for treating disease amenable to treatment with a phenidate drug in a patient in need of such treatment comprising administering to the patient a dosage form of a pharmaceutically acceptable salt of d-threo-methylphenidate, said dosage form providing an in vitro release profile comprising two pulses of drug release, wherein said pulses are temporally separated by from about 2 hours to about 7 hours.

11. A method for treating disease amenable to treatment with a phenidate, drug in a patient in need of such treatment comprising administering to the patient a dosage form of a pharmaceutically acceptable salt of d-threo-methylphenidate providing an in vivo plasma concentration of said d-threo-methylphenidate comprising two maxima, wherein said maxima are temporally separated by from about 2 hours to about 7 hours, and wherein the magnitude of said maxima differ by no more than about 30 percent.

* * * * *

UNITED STATES PATENT AND TRADEMARK OFFICE
CERTIFICATE OF CORRECTION

PATENT NO. : 6,635,284 B2  
DATED : October 21, 2003  
INVENTOR(S) : Atul M. Mehta, Andrew L. Zeitlin and Maghsoud M. Dariani It is certified that error appears in the above-identified patent and that said Letters Patent is hereby corrected as shown below:

Column 8,
Line 62, delete "Hüils" and insert -- Hüls --.

Signed and Sealed this

Fifteenth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,635,284 B2
DATED : October 21, 2003
INVENTOR(S) : Atul M. Mehta, Andrew L. Zeitlin and Maghsound M. Dariani It is certified that error appears in the above-identified patent and that said Letters Patent is hereby corrected as shown below:

Title page,
Item [73], Assignee, delete "Celegene" and insert -- Celgene --

Signed and Sealed this

Fifth Day of April, 2005

JON W. DUDAS
*Director of the United States Patent and Trademark Office*